United States Patent [19]

Perregaard et al.

[11] Patent Number: 5,439,922
[45] Date of Patent: Aug. 8, 1995

[54] PIPERIDYL-SUBSTITUTED INDOLES FOR TREATING ANXIETY

[75] Inventors: Jens K. Perregaard, Jaegerspris, Denmark; Brenda Costall, Bradford, England

[73] Assignee: H. Lundbeck A/S, Copenhagen-Valby, Denmark

[21] Appl. No.: 999,482

[22] Filed: Dec. 17, 1992

Related U.S. Application Data

[63] This is a continuation of PCT/DK91/00168, filed Jun. 21, 1991.

Foreign Application Priority Data

Jun. 22, 1990 [DK] Denmark ................ 1520/90

[51] Int. Cl.⁶ ............ A61K 31/445; C07D 401/14; C07D 403/14; C07D 403/04
[52] U.S. Cl. .................. 514/323; 514/256; 514/316; 514/318; 514/324; 514/339; 546/193; 546/201; 546/256; 546/257; 546/262; 546/273; 544/335
[58] Field of Search ............ 544/335; 546/193, 201, 546/256, 257, 202, 273; 514/256, 316, 318, 323, 324, 339

[56] References Cited

U.S. PATENT DOCUMENTS

| | | | |
|---|---|---|---|
| 4,710,500 | 12/1987 | Perregaard | 546/257 |
| 4,997,841 | 5/1991 | Oxford | 514/323 |
| 5,036,078 | 7/1991 | Coates | 514/323 |
| 5,216,001 | 6/1993 | Perregaard | 546/201 |

FOREIGN PATENT DOCUMENTS

| | | |
|---|---|---|
| 0007258 | 1/1980 | European Pat. Off. |
| 1438094 | 6/1976 | United Kingdom |

OTHER PUBLICATIONS

Skarsfeldt et al., "Sertindole, a new neuroleptic ...", CA 113:109264s (1990).
Ueda et al., "Preparation of (piperidinoalkyl)thiazoles as antiallergy agents", CA 107:236692f (1987).

*Primary Examiner*—Ceila Chang
*Attorney, Agent, or Firm*—Darby & Darby

[57] ABSTRACT

A method for treating anxiety in mammals comprising administering in an effective amount to said mammal an 1-aryl-3-(4-piperidyl)-indole derivative having the general formula:

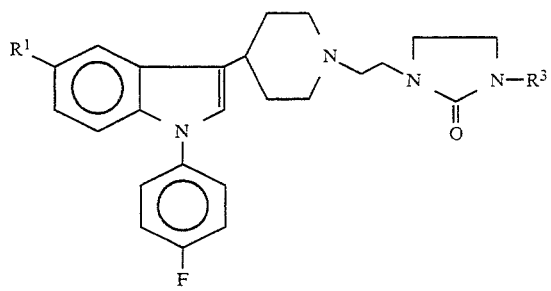

wherein $R^1$ is H, F, Cl, Br, methyl, methoxy or cyano; and $R^3$ is H or methyl; or a pharmaceutical acceptable acid addition salt thereof.

1 Claim, No Drawings

PIPERIDYL-SUBSTITUTED INDOLES FOR TREATING ANXIETY

This is a continuation of international application Ser. No. PCT/DK91/00168, filed 21 Jun. 1991.

The present invention relates to the use of a class of 1-aryl-3-(4-piperidyl)-indole derivatives for the manufacture of medicaments for the treatment of anxiety in mammals, including humans, and certain of the compounds used which are novel compounds.

U.S. Pat. No 4,710,500 corresponding to European patent No 0200322 discloses in general optionally 5-substituted 1-aryl-3-(4-piperidyl)-(I'), 1-aryl-3- (1-piperazinyl)- (II), or 1-aryl-3-(1,2,3,6-tetrahydro-4-pyridyl)indole (III) derivatives having the formulas:

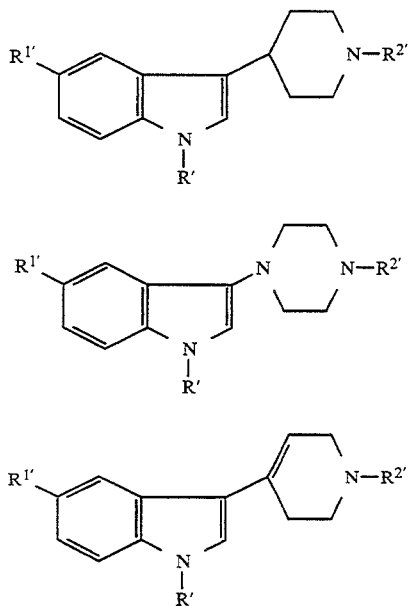

The compounds are claimed to be potent and long-lasting dopamine antagonists, and accordingly to be useful in the treatment of psychoses and additionally to be strong 5-HT$_2$ antagonists indicating effects in the treatment of negative symptoms of schizophrenia and depression and cardiovascular diseases. One of the tests used to show blockade of dopaminergic activity was a catalepsy test, catalepsy being at that time regarded as a test for antidopaminergic activity. However, at present catalepsy is considered to be a measure of the propensity of an antipsychotic compound to induce extrapyramidal side effects.

Today therapeutical treatment with benzodiazepines almost reign supreme for the treatment of anxiety. However, though they show activity against anxiety, the benzodiazepines have severe well known side effects. The most important of these side effects are sedation, dizziness, balance disturbances, interaction with alcohol, amnesia and a rapid addiction or habituation. As a consequence the use of the benzodiazepines in the treatment of anxiety has become controversial, and accordingly there is a strong need for new means for the treatment of anxiety.

Surprisingly, it has now been found that certain 1-aryl-3-(4-piperidyl)-indole derivatives having the above formula I' have very potent anxiolytic activity substantially without the side effects mentioned and that they are without or only have weak cataleptogenic activity, thereby being useful in the treatment of anxiety.

Accordingly, the present invention provides the use of an 1-aryl-3-(4-piperidyl)-indole derivative having the generel formula:

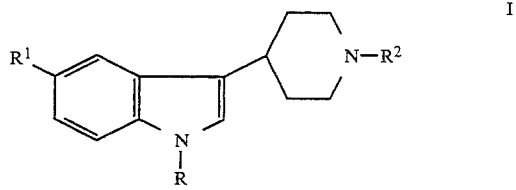

wherein

R$^1$ is hydrogen, halogen, lower alkyl, lower alkoxy, hydroxy, cyano, nitro, lower alkylthio, trifluoromethyl, trifluoromethylthio, lower alkylsulfonyl, amino, lower alkylamino or lower dialkylamino;

R is phenyl optionally substituted with one or more substituents independently selected from the following: halogen, lower alkyl, lower alkoxy, hydroxy, trifluoromethyl, and cyano, or R is a hetero aromatic group, preferably 2-thienyl, 3-thienyl, 2-furanyl, 3-furanyl, 2-thiazolyl, 2-oxazolyl, 2-imidazolyl, 2-pyridyl, 3-pyridyl, or 4-pyridyl; and R$^2$ is hydrogen, cycloalkyl, cycloalkylmethyl, lower alkyl or lower alkenyl, optionally substituted with one or two hydroxy groups, any hydroxy group present being optionally esterified with an aliphatic carboxylic acid having from two to twentyfour carbon atoms inclusive, or R$^2$ is a group of the formula IV:

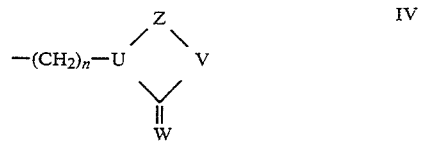

wherein n is an integer from 2-6;

W is oxygen, or sulphur;

U is nitrogen or carbon;

Z is —(CH$_2$)$_m$—, m being 2 or 3, or Z is —CH═CH— or 1,2-phenylene optionally substituted with halogen or trifluoromethyl, or Z is —COCH$_2$— or —CSCH$_2$—;

V is oxygen, sulphur, CH$_2$, or NR$^3$, wherein R$^3$ is hydrogen, lower alkyl or lower alkenyl optionally substituted with one or two hydroxy groups, or a cycloalkyl or cycloalkylmethyl group;

or a pharmaceutically acceptable acid addition salt thereof for the manufacture of a medicament for therapeutical treatment of anxiety in mammals, including humans.

The term "lower alkyl" is intended to mean a straight or branched alkyl group having from one to four carbon atoms, such as methyl, ethyl, n-propyl, iso-propyl, n-butyl, sec-butyl, etc. Lower alkoxy, lower alkylthio, lower alkylsulfonyl, lower alkylamino and lower dialkylamino similarly designate such groups wherein the alkyl moiety is a lower alkyl group as defined above.

Lower alkenyl is intended to mean an alkenyl group containing from 2 to 4 carbon atoms, for example ethenyl, 1-propenyl, 2-butenyl, etc., and cycloalkyl is a cyclic alkyl group having from three to six carbon atoms inclusive The pharmaceutically acceptable acid addition salts of the compounds used in the invention are salts formed with non-toxic organic or inorganic acids. Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids.

The compounds of the formula I and the pharmaceutically acceptable acid addition salts thereof may be administered in any suitable way, e.g. orally or parenterally, and the compounds may be presented in any suitable form for such administration, eg. in the form of tablets, capsules, powders, syrups or solutions or dispersions for injection.

An effective daily dose of a compound of the formula I or a pharmaceutically acceptable salt thereof is from 1.0 ng/Kg to 1.0 mg/Kg body weight.

The compounds used in accordance with the present invention have been shown to be highly active in animal models predictive of anxiolytic effects in man and they have been found not to induce catalepsy or only induce weak catalepsy which today is regarded as an indication of extrapyramidal side effects. It is indeed very surprising that the present compounds are non-cataleptogenic whereas the compounds of the formulas II and III of the above US patent have proved to be cataleptogenic (c.f. the pharmacological data in the following). The mechanisms behind this are not fully understood.

In addition to the benzodiazepines other compounds which have proven to be or are potentially effective in the treatment of anxiety in humans and are active in some animal models indicative of anxiety are buspirone (a partial 5-$HT_{1A}$ agonist), ritanserin (a 5-$HT_2$ antagonist) and ondansetron (a selective 5-$HT_3$ antagonist). However said compounds are completely different from the present compounds in structure and their mechanisms of action seems to be different from those of the present compounds (c.f. the description of the pharmacology in the following).

In a preferred embodyment of the invention the compound used is a compound of the formula I as defined in the foregoing wherein R is phenyl substituted with halogen, or R is 2- or 3-thienyl;

$R^1$ is hydrogen, halogen, lower alkyl, lower alkoxy, cyano, trifluoromethyl, or lower alkylsulphonyl;

$R^2$ is a group having the formula IV as defined in the foregoing wherein n=2–6;

W is oxygen or sulphur;

U is nitrogen;

Z is —$(CH_2)_2$—, —$(CH_2)_3$—, or —CH=CH—; and

V is oxygen, $CH_2$ or $NR^3$, $R^3$ being hydrogen or lower alkyl;

or a pharmaceutically acceptable acid addition salt thereof.

Most preferably the compound used is a compound having the general formula I as defined above, wherein:

R is phenyl substituted in 4 position with fluoro; $R^1$ is hydrogen, halogen, or lower alkyl; $R^2$ is a group having the formula IV as defined in the foregoing wherein n=2; W is oxygen; U is nitrogen; Z is —$(CH_2)_2$—; and V is $NR^3$, $R^3$ being hydrogen or lower alkyl; or a pharmaceutically acceptable acid addition salt thereof.

Though U.S. Pat. No 4,710,500 generally comprises the 3-(4-piperidyl)-compounds of the formula I mentioned above, only five compounds have been specifically mentioned.

Accordingly the present invention also provides the novel 1-aryl-3-(4-piperidyl)-indole derivatives having the generel formula I as defined above, provided that in case R is 4-fluorophenyl: $R^2$ may not be $CH_3$ when $R^1$ is $CH_3$ or $CF_3$, $R^1$ may not be hydrogen or chloro when $R^2$ is an 2-(2-imidazolidinon-1-yl)ethyl group and $R^1$ may not be $CF_3$ when $R^2$ is an 2-(1-pyrrolidin-2-on-yl)ethyl group; and pharmaceutically acceptable acid addition salts thereof.

The compounds of the formula I used in the invention may be prepared according to methods (b), (c), or (d) described in U.S. Pat. No. 4,710,500. 2-pyrrolidinthiones are prepared from the corresponding lactame derivatives according to litterature methods (Bull.Soc.-Chim.Belg. 87, 223, 229, 299, 525 (1978)) by using Lawesson's reagent or phosphorous pentasulphide at appropriate temperatures. Imidazolidin-2-thion derivatives are prepared by ringclosure reactions from properly substituted ethylendiamines with carbondisulphide, thiophosgen or corresponding thiocarbonyl precursor compounds.

When $R^1$ is hydroxy the compound may be prepared by conventional methods of demethylation of the corresponding methyl ether. Pyridine hydrochloride, hydrobromic acid or methionine in methanesulphonic acid may be used to split off the methyl group.

The compounds wherein $R^1$ is cyano may be prepared by substitution of 5-bromo or 5-iodo in the appropriate substituted compounds using CuCN in an aprotic polar solvent such as N,N-dimethyiformamide, N-methyl-2-pyrrolidone (NMP) or HMPA at elevated temperatures.

In compounds wherein $R^3$ is hydroxy substituted alkyl the hydroxy group may be introduced by deprotection of a corresponding labile ether derivative, eg. by treating the benzyl ether in strong mineral acid, such as hydrobromic acid, or by catalytic debenzylation using Pd or Pt as catalyst.

The acid addition salts of the compounds used in the invention are easely prepared by methods well known in the art. The base is reacted with either the calculated amount of organic or inorganic acid in an aqueous miscible solvent, such as acetone or ethanol, with isolation of the salt by concentration and cooling, or an excess of the acid in an aqueous immiscible solvent such as ethyl ether or chloroform with the desired salt separating directly. Of course, these salts may also be prepared by the classical method of double decomposition of appropriate salts.

The following compounds were prepared according to methods (b), (c), or (d) described in U.S. Pat. No. 4,710,500 or from the corresponding lactame derivatives according to litterature methods (Bull.Soc.Chim.-Belg. 87,223, 229, 299, 525 (1978)) by using Lawesson's reagent or phosphorous pentasulphide at appropriate temperatures:

1-(4-fluorophenyl)-5-methyl-3-(1-methyl-4-piperidyl)-1H-indole, hydrobromide, Lu 21-037, MP: 254°–256° C.

1-(4-fluorophenyl)-3-[1-[2-(2-imidazolidinon-1-yl)ethyl]-4-piperidyl]-1H-indole, Lu 23-086, MP: 174°–175° C.

1-(4-fluorophenyl)-3-[1-[2-(2-pyrrolidinon-1-yl)ethyl]-4-piperidyl]-5-trifluoromethyl-1H-indole, fumarate, Lu 23-158, MP: 240°–241° C.

1-(4-fluorophenyl)-3-(1-methyl-4-piperidyl)-5-trifluoromethyl-1H-indole, oxalate, Lu 21-131, MP: 251°–252° C.

5-chloro-1-(4-fluorophenyl)-3-[1-[2-(2-imidazolidinon-1-yl)ethyl]-4-piperidyl]-1H-indole, Lu 23-174, MP:162° C.

5-chloro-1-(4-fluorophenyl)-3-[1-(2-hydroxyethyl)-4-piperidyl]-1H-indole, hydrochloride, 1 MP:266°–269° C.

5-chloro-1-(4-fluorophenyl)-3-[1-[2-(2-oxazolidinon-1-yl)ethyl]-4-piperidyl]-1H-indole, fumarate, 2, MP: 203°–205° C.

5-chloro-1-(4-fluorophenyl)-3-[1-[2-(3-methyl-2-imidazolidinon-1-yl)ethyl]-4-piperidyl]1H-indole, fumarate, 3, MP: 198°–199° C.

5-chloro-1-(4-fluorophenyl)-3-[1-[2-(2-pyrrolidinon-1-yl)ethyl]-4-piperidyl]-1H-indole, fumarate, 4, MP: 209°–211° C.

1-(4-fluorophenyl)-3-[1-[2-(3-methyl-2-imidazolidinon-1-yl)ethyl]-4-piperidyl]-5-trifluoromethyl-1H-indole, 5, MP: 144°–145° C.

1-(4-fluorophenyl)-3-[1-[2-(2-oxazolidinon-1-yl)ethyl]-4-piperidyl]-1H-indole, fumarate, 6, MP: 212°–213° C.

5-chloro-1-(4-fluorophenyl)-3-[1-[2-(2-pyrrolidinthion-1-yl)ethyl]-4-piperidyl]-1H-indole, fumarate, 7, MP: 195°–199° C.

1-(4-fluorophenyl)-3-[1-[2-(2-imidazolidinon-1-yl)ethyl]-4-piperidyl]-5-methyl-sulfonyl-1H-indole, fumarate, 8, MP: 188°–192° C.

5-chloro-1-(4-fluorophenyl)-3-[1-[6-(2-pyrrolidinon-1-yl)-1-hexyl]-4-piperidyl]-1H-indole, hydrochloride, 9, MP: 123°–128° C.

5-chloro-1-(4-fluorophenyl)-3-(4-piperidyl)-1H-indole, fumarate, 10, MP: 196°–201° C.

1-(4-fluorophenyl)-3-(4-piperidyl)-5-trifluoromethyl-1H-indole, hydrochloride, 11 MP: 281°–284° C.

1-(4-fluorophenyl)-3-[1-[2-(2-imidazolidinon-1-yl)ethyl]-4-piperidyl]-5-trifluomethyl-1H-indole, 12, MP:169°–171° C.

1-(4-fluorophenyl)-3-[1-[6-(2-pyrrolidinon-1-yl)-1-hexyl]-4-piperidyl]-5-trifluoromethyl-1H-indole,oxalate, 13, MP: 85°–87° C.

5-chloro-1-(4-fluorophenyl)-3-[1-[2-[3-(2-propyl)-2-imidazolidinon-1-yl]ethyl]-4-piperidyl]-1H-indole, oxalate, 14, MP :92°–96° C.

5-fluoro-1-(4-fluorophenyl)-3-(4-piperidyl)-1H-indole, fumarate, 15, MP:198°–200° C.

5-fluoro-1-(4-fluorophenyl)-3-[1-[2-(2-imidazolidinon-1-yl)ethyl]-4-piperidyl]-1H-indole, oxalate, 16, MP: 188°–190° C.

5-fluoro-1-(4-fluorophenyl)-3-[1-[2-(2-pyrrolidinon-1-yl)ethyl]-4-piperidyl]-1H-indole, fumarate, 17, MP : 178°–180° C.

5-fluoro-1-(4-fluorophenyl)-3-[1-[2-[3-(2-propyl)-2-imidazolidinon-1-yl]ethyl]-4-piperidyl]-1H-indole, fumarate, 18, MP: 115°–120° C.

5-chloro-1-(4-fluorophenyl)-3-[1-[5-(2-imidazolidinon-1-yl)-1-pentyl]-4-piperidyl]-1H-indole, oxalate, 19, MP: 145°–147° C.

5-chloro-1-(4-fluorophenyl)-3-[1-[4-(2-imidazolidinon-1-yl)-1-butyl]-4-piperidyl]-1H-indole, oxalate, 20, MP: 178°–179° C.

5-chloro-1-(4-fluorophenyl)-3-[1-[6-(2-imidazolidinon-1-yl)-1-hexyl]-4-piperidyl]-1H-indole, oxalate, 21, MP: 156°–158° C.

5-chloro-1-(4-fluorophenyl)-3-[1-[2-(hydantoin-2-yl)ethyl]-4-piperidyl]-1H-indole, 22, MP: 174°–176° C.

5-fluoro-1-(4-fluorophenyl)-3-[1-[6-(2-pyrrolidinon-1-yl)-1-hexyl]-4-piperidyl]-1H-indole, 23, oil 1-(4-fluorophenyl)-3-[1-[2-(2-imidazolidinon-1-yl)ethyl]-4-piperidyl]-5-methyl-1H-indole, 24, MP: 187°–189° C.

1-(4-fluorophenyl)-3-[1-[2-[3-(2-propyl)-2-imidazolidinon-1-yl]ethyl]-4-piperidyl]-5-methyl-1H-indole, hydrochloride, hydrate, 25, MP:214°–215° C.

1-(4-fluorophenyl)-3-[1-[2-(2-pyrrolidinon-1-yl)ethyl]-4-piperidyl]-5-methyl-1H-indole, hydrochloride, hemihydrate, 26, 265°–266° C.

1-(4-fluorophenyl)-3-[1-[2-[3-(2-propyl)-2-imidazolidinon-1-yl]ethyl]-4-piperidyl]-5-trifluoromethyl-1H-indole, 27, MP: 99°–100° C.

3-[1-[2-(2-imidazolidinon-1-yl)ethyl]-4-piperidyl]-1-(3-thienyl)-1H-indole, oxalate 28, MP: 139°–140°

1-(4-fluorophenyl)-3-[1-[2-(2-imidazolidinon-1-yl)ethyl]-4-piperidyl]-5-methoxy-1H-indole, 29, MP: 167° C.

5-fluoro-3-[1-[2-[3-(2-propyl)-2-imidazolidinon-1-yl]ethyl]-4-piperidyl]-1-(3-thienyl)-1H-indole, oxalate, hemihydrate. 30, MP: 95°–97° C.

5-fluoro-3-[1-[2-[3-(2-propyl)-2-imidazolidinon-1-yl]ethyl]-4-piperidyl]-1-(2-thienyl)-1H-indole, dioxalate, 31, MP: 173°–174° C.

5-bromo-1-(4-fluorophenyl)-3-[1-[2-(2-imidazolidinon-1-yl)ethyl]-4-piperidyl]-1H-indole, 32, MP: 171°–172° C.

1-(4-fluorophenyl)-3-[1-[2-[3-(2-propyl)-2-imidazolidinon-1-yl]ethyl]-4-piperidyl]-1H-indole, hydrochloride, 33, MP: 226°–227° C.

5-chloro-1-(4-fluorophenyl)-3-[1-[3-(2-imidazolidinon-1-yl)-1-propyl]-4-piperidyl]-1H-indole, fumarate, 34, MP: 203°–205° C.

5-chloro-1-(4-fluorophenyl)-3-[1-[2-[3-(2-hydroxyethyl)-2-imidazolidinon-1-yl]ethyl]-4-piperidyl]-1H-indole, fumarate, 38, MP: 180°–182° C.

In the following example the preparation of compounds used in accordance whith the invention is further illustrated by way of examples:

EXAMPLE 1

5-chloro-1-(4-fluorophenyl)-3-[1-[2-(2-imidazolidinthion-1-yl)ethyl]-4-piperidyl]-1H-indole, oxalate, 35, MP: 150° C.

To a solution of 5-chloro-1-(4-fluorophenyl)-3-(4-piperidyl)-1H-indole (25 g) in N-methyl-2-pyrrolidone (150 ml) were added chloroacetonitrile (6 g) and triethylamine (10 ml). The reaction mixture was heated at 60° C. for one hour and subsequently poured onto crushed ice. The precipitated 5-chloro-3-(1-cyanomethyl-4-piperidyl)-1-(4-fluorophenyl)-1H-indole was filtered off and washed with water. Yield 20 g. MP:170°–172° C.

A solution of the thus isolated cyanomethylderivative (24 g) in dry THF (150 ml) was added dropwise to a previously prepared solution of AlH$_3$ (from 8 g of LiAlH$_4$ and 8 g of AlCl$_3$) in dry diethyl ether (250 ml). The mixture was heated at reflux for one hour and finally hydrolyzed by carefully adding a conc. aqueous solution of NaOH (10 ml) under simultaneous cooling.

Inorganic salts were filtered off and were subsequently carefully washed with hot dichloromethane (2×100 ml). The combined organic phases were dried (anh. MgSO₄) and finally evaporated leaving 3-[1-(2-aminoethyl)-4-piperidyl]-5-chloro-1-(4-fluorophenyl)-1H-indole (25 g) as an oil.

Without further purification this product (12 g) and triethylamine (4.2 g) were heated in 1,1,1-trichloroethane (100 ml) at 50°–55° C. A solution of chloroacetonitrile (3.6 g )in 1,1,1-trichloroethane (10 ml) was added dropwise during 10 minutes. The mixture was heated for another 4 hours at 50° C. Ethyl acetate (200 ml) was added and the mixture was poured into ice cooled dil. aqueous NaOH solution (400 ml). The organic phase was separated, washed with brine, dried (anh. MgSO₄) and the solvents evaporated leaving 5-chloro-3-[1-[2-(N-cyanomethyl)aminoethyl]-4-piperidyl]-1-(4-fluorophenyl)-1H-indole (14 g) as an oil.

The oil thus isolated was dissolved in dry THF (100 ml) and added dropwise to a previously prepared solution of AlH₃ (from 6 g of LiAlH₄ and 6 g of AlCl₃)in dry diethyl ether (200 ml). The mixture was refluxed for one hour and finally hydrolyzed by cautiously adding a conc. aqueous solution of NaOH (8 ml) under simultaneous cooling. Inorganic salts were filtered off and were subsequently washed with hot dichloromethane (2×100 ml). The combined organic phases were dried (anh. MgSO₄) and finally evaporated leaving 3-[1-[N-(2-aminoethyl)-2-aminoethyl]-4-piperidyl]-5-chloro-1-(4-fluorophenyl)-1H-indole (8.5 g) as an oil. This oil (4.5 g) was dissolved in 1-pentanol (50 ml) and carbondisulphide (5 ml) was added. After stirring for 2 hours at room temperature the resulting suspension was heated to 140° C. for 1.5 hours. Excess CS₂ was flushed away by a gentle stream of N₂ gas. Finally most of the 1-pentanol was evaporated at reduced pressure. The remaining oil was purified by column chromatography on silica gel (eluted with ethyl acetate/ethanol/triethylamine—80/20/4). The oxalate salt of the title compound 35 crystallized from acetone. Yield 250 mg. MP: 150° C.

EXAMPLE 2

1-(4-Fluorophenyl)-5-hydroxy-3-[1-[2-(2-imidazolidinon-1-yl)ethyl]-4-piperidyl]-1H-indole, 36, MP: 220° C.

Pyridinhydrochloride (60 g) and 1-(4-fluorophenyl)-3-[1-[2-(2-imidazolidinon-1-yl)ethyl]-4-piperidyl]-5-methoxy-1H-indole, compound 29, (6 g) were mixed and heated to 180° C. under N₂ for 1½ hours. After cooling, water (300 ml) and ethyl acetate (100 ml) were added. By addition of NH₄OH solution the pH was adjusted to >9. The organic phase was separated, washed with water (50 ml), dried (anh. MgSO₄), and the solvent evaporated leaving the phenolic crude title compound as an oil. Purification by column chromatography on silica gel (eluted with ethyl acetateldichloromethane/ethanol/triethylamine 60:20:20:5) afforded the title compound 36 as a crystalline material. Yield: 1.9 g. MP: 220° C.

EXAMPLE 3

5-Cyano-1-(4-fluorophenyl)-3-[1-[2-(2-imidazolidinon-1-yl)ethyl]-4-piperidyl]-1H-indole, 37, MP: 209° C.

To a solution of 5-bromo-1-(4-fluorophenyl)-3-(4-piperidyl)-1H-indole (17 g) in dichloromethane (170 ml) was added a solution of di-tert.-butyloxycarbonate (12 g) in dichloromethane (30 ml). After stirring for 30 minutes at room temperature the dichloromethane was evaporated in vacuo. 5-Bromo-3-(1-tert-butyloxycarbonyl-4-piperidyl)-1-(4-fluorophenyl)-1H-indole crystallized from n-heptane. Yield: 14 g. MP: 155° C. All the crystalline material was dissolved in N-methyl-2-pyrrolidone (75 ml) and CaCN (5 g) was added. The mixture was heated at 160° C. for 6 hours. The mixture was then poured into a solution of NaCN (10 g)in water (200 ml) and stirred for 20 minutes. Diethyl ether (200 ml) was added. The ether phase was separated, washed with brine (50 ml), dried (anh. MgSO₄), and the ether evaporated leaving a mixture of 5-bromo and 5-cyano compounds which were separated by column chromatography on silica gel (eluted with diethyl ether). The 3-(1-tert.butyloxycarbonyl-4-piperidyl)-5-cyano-1-(4-fluorophenyl)-1H-indole was isolated an an oil. Yield: 4.5 g. The protecting group—tert.butyloxycarbonyl—was splitted off by standard acidic (CF₃COOH) decomposition. The thus obtained 5-cyano-1-(4-fluorophenyl)-3-(4-piperidyl)-1H-indole (3.2 g) was dissolved in methyl isobutyl ketone (90 ml). Potassium carbonate (4.5 g), potassium iodide (0.5 g) and 1-(2-chloroethyl)-2-imidazolidinone (2.3 g) were added. The mixture was refluxed for 16 hours. After cooling inorganic salts were filtered off, and the organic solvent evaporated. Water (100 ml) and ethyl acetate (50 ml) were added. The organic phase was separated, dried (anh. MgSO₄), and finally ethyl acetate evaporated leaving the crude title compound as an oil. Purification by column chromatography on silica gel (eluted with ethyl acetate/ethanol/triethylamine 80:20:4) afforded 2.1 g of pure crystalline title compound, 37. MP: 209° C.

PHARMACOLOGY

The compounds used in the invention were tested in accordance with well recognized and reliable test methods. The tests were as follows:

CATALEPSY TEST

Evaluation of catalepsy was made according to Arnt (Eur. J. Pharmacol. 90, 47–55 (1983)). Catalepsy is an indicator of dopamine receptor blockade in vivo which corrolates to the clinical potency of the classical neuroleptics. However, catalepsy is also considered to indicate extrapyramidal side effects (Arnt, J. et al.; *Neuropharrnacology* 1981, 20, 1331–1334.

Procedure

In this test test compound is given s.c. in different doses. The rat (170–240 g )is placed on a vertical wire mesh ( mesh diameter 12 mm ). The rat is considered cataleptogenic if it remains immobile for more than 15 sec. The maximum number of rats showing catalepsy within the first 6 hours is recorded for each dose group. The results are recorded in fractions and an ED₅₀ value is calculated by means of log-probit analysis. The results are shown in Table 1.

The following corresponding 1-aryl-3-(1,2,3,6-tetrahydropyridyl)- or 1-aryl-3-(piperazinyl)indole derivatives which are analogues of Lu 23–174 and Compound No 12, respectively, were included in the test as comparing compounds:

A) 1-(4-Fluorophenyl)-3-[1-[2-(2-imidazolidinon-1-yl)ethyl]-1,2,3,6-tetrahydropyridin-4-yl]-5-trifluoromethyl-1H-indole B) 5-Chloro-1-(4-fluorophenyl)-3-[1-[2-(2-imidazolidinon-1-yl)ethyl]-1,2,3,6-tetrahydro-4-pyridyl]-1H-indole C) 5-Chloro-1-(4-fluorophenyl)-3-[4-[2-(2-imidazolidinon-1-yl)ethyl]-1-piperazinyl]-1H-indole

TABLE 1

| Compound | $ED_{50}$ (s.c.) (μmol/kg) |
| --- | --- |
| Lu 23-174 | >98 |
| comp. No 12 | 38 |
| comp. No 2 | >18 |
| comp. No 3 | 31 |
| comp. No 4 | 23 |
| comp. No 14 | >69 |
| comp. No 16 | >78 |
| comp. No 24 | >95 |
| comp. A | 0.49 |
| comp. B | 2.2 |
| comp. C | 4.5 |

Further $ED_{50}$ values of corresponding 1-aryl-3-(1,2,3,6-tetrahydro-4-pyridyl)- or 1-aryl-3-(1-piperazinyl)indole derivatives are given in U.S. Pat. No. 4,710,500.

LIGHT/DARK DISCRIMATION TEST IN MICE

This test was carried out in accordance with the method described in Costall et al. Br. J. Pharmacol. 90 275P (1987).

The test was conducted using a two compartment activity box in which the actions of anxiolytic compounds to reduce aversion against a brightly-lit environment may be readily detected. The box is designed as an open-top experimental box (45*27*27 cm) one third of which was partitioned from the rest, painted black and illuminated with red light. The remainder of the box was painted white and brightly illuminated (1000 W). The floor of each area was lined into squares. Behavioural changes were determined for each area from video recordings for periods of 40 min. Data obtained from dose groups of 5 animals (male albino BKW mice, 25–30 g) were analysed using single factor analysis of variance, and Dunnett's t-test. Test compounds were given intrapentoneally 45 min before testing.

The results are given in the following Table 2 as minimum doses (mg/kg i.p.) tested showing effect ($p<0.001$). The behavioural change used were exploratory rearings and line crossings.

The known substances diazepam, and ondansetron were included in the test for comparison purposes.

TABLE 2

| Compound | Rearings Minimum effective dose (μg/kg) | Line crossings Minimum effective dose (μg/kg) |
| --- | --- | --- |
| No 16 | 0.001 < ME < 0.1 | 0.001 < ME < 0.1 |
| No 3 | 0.001 | 0.001 |
| Lu 23-174 | 0.000001 | 0.000001 |
| Diazepam | 0.13 | 0.13 |
| Odansetron | 0.05 | 0.05 |

The well known 5-$HT_2$ antagonist ritanserin did not show effect in this test.

LIGHT/DARK DISCRIMINATION TEST IN RATS

The test was carried out similarly to the test in mice described above, however modified in accodance with F. C. Colpaert et al., Psychopharmacology (1985) 86: 45–54. The test used Wistar WU rats.

In this test the compound Lu 23-174 according to the invention showed effect in nano molar doses/kg (s.c.; observation 2h).

The well known 5-$HT_2$ antagonist ritanserin was only active in μmolar doses/kg.

INHIBITION OF AGGRESSION IN MICE

This test is used to evaluate the ability of a test substance to inhibit isolation induced aggressive behaviour in mice and is considered to be a test model for anxiolytic effect. The method is a modified version of the method described by McMillen et al. in Drug Develop. Research 12, 53–62, 1988.

Procedure

Male mice (NMRI/BOM,SPF) weighing 16–18 g were used. The mice were housed individually in macrolon cages for 3 weeks before training to attack an intruder mouse. The mice were trained daily for a period of 1–2 weeks until a satisfactory respons was obtained. During the first days the mice were trained against each other. When a satisfactory respons was obtained group-housed mice were used as intruders. The time elapsed until attack was recorded. The intruder mouse was removed as soon as an attack had occured or after 180 sec. After the training period 60–70 percent of the mice had latencies of less than 10 sec.

The mice were pretested before drug treatment. Only mice attacking within 25 sec. were used. The animals were treated with test substance or saline. The mice were tested 30 or 120 minutes later, respectively. Non-specific motoric effects were also recorded. 8 mice were used per group.

The results were stated as fractions of mice with attack latencies greater than or equal to a threshold value. As threshold values were used 180 and 90 sec. $ED_{50}$ values were calculated by log-probit analysis.

The results are given in the following table as $ED_{50}$ values in in μmol/kg. The known compounds diazepam, buspirone and ritanserin were included in the test for the purpose of comparison.

TABLE 3

| | Threshold Value $ED_{50}$ (μmol/kg) | | | |
| --- | --- | --- | --- | --- |
| | 30 min Pretreatment | | 120 min Pretreatment | |
| Compound | 90 sec. | 180 sec. | 90 sec. | 180 sec. |
| Lu 23-174 | 4.4 | 3.2 | | |
| Lu-23-086 | | | 1.9 | 1.7 |
| Compound No 16 | | | 2.1 | 1.6 |
| Compound No 24 | | | 3.2 | 2.5 |
| Diazepam | 26 | 15 | | |
| Buspirone | 9.6 | 5.4 | | |
| Ritanserin | >21 | >21 | >10 | >10 |

It appears from the above results that the compounds used in the present invention have very weak or no cataleptic effect and have potent anxiolytic effects. So it is seen from table 1 that the cataleptic effects are much weaker than those of the corresponding 1-aryl-3-(1,2,3,6-tetrahydrpyridyl)- or 1-aryl-3-(piperazinyl)indole derivatives (a factor of about 100).

Furhermore the results show that the present compounds have much more potent anxiolytic effects than diazepam (until 5 orders of magnitude in the mouse dark/light discrimination test and a factor 6–10 in the aggression test).

In the light/dark discrimination test in mice the present compounds are very potent (effect in nano molar doses) whereas the well known 5$HT_2$ antagonist ritanserin is inactive. Additionally ritanserin showed no effect in the aggression test. This shows that the anxiolytic activity cannot be a consequence of the 5HT$_2$ action alone.

Furthermore, the compounds used in the present invention appear to be more potent than the substances proven to be effective in humans, such as benzodiazepines and buspirone, and the recent potential anxiolytics, such as ritanserin and ondansetron.

FORMULATION EXAMPLES

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting maschine. Examples of adjuvants or diluents comprise: corn starch, potato starch, talcum, magnesium stearate, gelatine, lactose, gums, and the like. Any other adjuvant or additive colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilization of the solution and filling in suitable ampules or vials. Any suitable additive conventionally used in the art may be added, such as tonicity agents, preservatives, antioxidants, etc.

Typical examples of recipes for the formulations of the invention are as follows:

| 1) | Tablets containing 0.5 milligrams of Lu 23-174 calculated as the free base: | |
|---|---|---|
| | Lu 23-174 | 0.5 mg |
| | Lactose | 18 mg |
| | Potato starch | 27 mg |
| | Saccharose | 58 mg |
| | Sorbitol | 3 mg |
| | Talcum | 5 mg |
| | Gelatine | 2 mg |
| | Povidone | 1 mg |
| | Magnesium stearate | 0.5 mg |
| 2) | Tablets containing 1 milligrams of compound No 3 calculated as the free base: | |
| | Comp. 3 | 1.0 mg |
| | Lactose | 16 mg |
| | Potato starch | 45 mg |

| | -continued | |
|---|---|---|
| | Saccharose | 106 mg |
| | Sorbitol | 6 mg |
| | Talcum | 9 mg |
| | Gelatine | 4 mg |
| | Povidone | 3 mg |
| | Magnesium stearate | 0.6 mg |
| 3) | Syrup containing per milliliter: | |
| | Comp. 16 | 5.0 mg |
| | Sorbitol | 500 mg |
| | Tragacanth | 7 mg |
| | Glycerol | 50 mg |
| | Methyl-paraben | 1 mg |
| | Propyl-paraben | 0.1 mg |
| | Ethanol | 0.005 ml |
| | Water | ad 1 ml |
| 4) | Solution for injection containing per milliliter: | |
| | Lu 23-174 | 0.2 mg |
| | Acetic acid | 17.9 mg |
| | Sterile water | ad 1 ml |
| 5) | Solution for injection containing per milliliter: | |
| | Comp. 3 | 0.5 mg |
| | Sorbitol | 42.9 mg |
| | Acetic acid | 0.63 mg |
| | Sodium hydroxide | 22 mg |
| | Sterile water | ad 1 ml |

We claim:

1. A method for treating anxiety in mammals comprising administering in an effective amount, to said mammal, an 1-aryl-3-(4-piperdyl)indole derivative having the general formula:

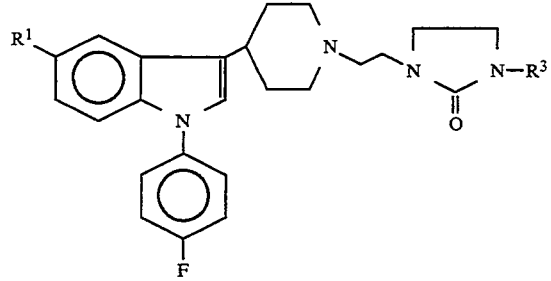

wherein $R^1$ is hydrogen, fluorine, chlorine, bromine, methyl, methoxy or cyano; wherein $R^3$ is hydrogen or methyl; or a pharmaceutically acceptable acid addition salt thereof.

* * * * *